(12) United States Patent
Goodacre

(10) Patent No.: US 6,914,060 B2
(45) Date of Patent: Jul. 5, 2005

(54) IMIDAZOTRIAZINONE DERIVATIVES AS LIGANDS FOR GABA RECEPTORS

(75) Inventor: Simon Charles Goodacre, Benington (GB)

(73) Assignee: Merck Sharp & Dohme Ltd., Hoddesdon ( * ) Notice: Subject to any disclaimer, the term of this patent is extended or adjusted under 35 U.S.C. 154(b) by 0 days.

(21) Appl. No.: 10/848,461

(22) Filed: May 18, 2004

(65) Prior Publication Data

US 2004/0235844 A1 Nov. 25, 2004

(30) Foreign Application Priority Data

May 22, 2003 (GB) .............................................. 0311859

(51) Int. Cl.⁷ ...................... C07D 487/04; A61K 31/53; A61P 25/22; A61P 25/08

(52) U.S. Cl. ........................................ 514/243; 544/184

(58) Field of Search ........................... 544/184; 514/243

(56) References Cited

PUBLICATIONS

Rudolph et al. Trends in Pharmacological Sciences. vol. 22(4) : 188–194, 2001.*

* cited by examiner

*Primary Examiner*—Venkataraman Balasubramanian
(74) *Attorney, Agent, or Firm*—J. Eric Thies; Melvin Winokur

(57) ABSTRACT

The present invention relates to imidazo[2,1-f]triazin-4-one analogues which are substituted in the 7-position by a substituted phenyl ring, being ligands for $GABA_A$ receptors and accordingly of benefit in the therapy of deleterious neurological disorders.

11 Claims, No Drawings

IMIDAZOTRIAZINONE DERIVATIVES AS LIGANDS FOR GABA RECEPTORS

CROSS REFERENCE TO RELATED APPLICATIONS

This application claims priority under 35 U.S.C. §119 from GB Application No. 0311859.3, filed May 22, 2003.

The present invention relates to a class of substituted imidazo-triazinone derivatives and to their use in therapy. More particularly, this invention is concerned with imidazo [2,1-f]triazin-4-one analogues which are substituted in the 7-position by a substituted phenyl ring. These compounds are ligands for $GABA_A$ receptors and are therefore useful in the therapy of deleterious neurological complaints.

Receptors for the major inhibitory neurotransmitter, gamma-aminobutyric acid (GABA), are divided into two main classes: (1) $GABA_A$ receptors, which are members of the ligand-gated ion channel superfamily; and (2) $GABA_B$ receptors, which may be members of the G-protein linked receptor superfamily. Since the first cDNAs encoding individual $GABA_A$ receptor subunits were cloned the number of known members of the mammalian family has grown to include at least six α subunits, four β subunits, three γ subunits, one δ subunit, one ε subunit and two ρ subunits.

Although knowledge of the diversity of the $GABA_A$ receptor gene family represents a huge step forward in our understanding of this ligand-gated ion channel, insight into the extent of subtype diversity is still at an early stage. It has been indicated that an α subunit, a β subunit and a γ subunit constitute the minimum requirement for forming a fully functional $GABA_A$ receptor expressed by transiently transfecting cDNAs into cells. As indicated above, δ, ε and ρ subunits also exist, but are present only to a minor extent in $GABA_A$ receptor populations.

Studies of receptor size and visualisation by electron microscopy conclude that, like other members of the ligand-gated ion channel family, the native $GABA_A$ receptor exists in pentameric form. The selection of at least one α, one β and one γ subunit from a repertoire of seventeen allows for the possible existence of more than 10,000 pentameric subunit combinations. Moreover, this calculation overlooks the additional permutations that would be possible if the arrangement of subunits around the ion channel had no constraints (i.e. there could be 120 possible variants for a receptor composed of five different subunits).

Receptor subtype assemblies which do exist include, amongst many others, α1β2γ2, α2βγ1, α2β2/3γ2, α3βγ2/3, α4βδ, α5β3γ2/3, α6βγ2 and α6βδ. Subtype assemblies containing an α1 subunit are present in most areas of the brain and are thought to account for over 40% of $GABA_A$ receptors in the rat. Subtype assemblies containing α2 and α3 subunits respectively are thought to account for about 25% and 17% of $GABA_A$ receptors in the rat. Subtype assemblies containing an α5 subunit are expressed predominantly in the hippocampus and cortex and are thought to represent about 4% of $GABA_A$ receptors in the rat.

A characteristic property of all known $GABA_A$ receptors is the presence of a number of modulatory sites, one of which is the benzodiazepine (BZ) binding site. The BZ binding site is the most explored of the $GABA_A$ receptor modulatory sites, and is the site through which anxiolytic drugs such as diazepam and temazepam exert their effect. Before the cloning of the $GABA_A$ receptor gene family, the benzodiazepine binding site was historically subdivided into two subtypes, BZ1 and BZ2, on the basis of radioligand binding studies. The BZ1 subtype has been shown to be pharmacologically equivalent to a $GABA_A$ receptor comprising the α1 subunit in combination with a β subunit and γ2. This is the most abundant $GABA_A$ receptor subtype, and is believed to represent almost half of all $GABA_A$ receptors in the brain.

Two other major populations are the α2βγ2 and α3βγ2/3 subtypes. Together these constitute approximately a further 35% of the total $GABA_A$ receptor repertoire. Pharmacologically this combination appears to be equivalent to the BZ2 subtype as defined previously by radioligand binding, although the BZ2 subtype may also include certain α5-containing subtype assemblies. The physiological role of these subtypes has hitherto been unclear because no sufficiently selective agonists or antagonists were known.

It is now believed that agents acting as BZ agonists at α1βγ2, α2βγ2 or α3βγ2 subtypes will possess desirable anxiolytic properties. Compounds which are modulators of the benzodiazepine binding site of the $GABA_A$ receptor by acting as BZ agonists are referred to hereinafter as "$GABA_A$ receptor agonists". The α1-selective $GABA_A$ receptor agonists alpidem and zolpidem are clinically prescribed as hypnotic agents, suggesting that at least some of the sedation associated with known anxiolytic drugs which act at the BZ1 binding site is mediated through $GABA_A$ receptors containing the α1 subunit. Accordingly, it is considered that $GABA_A$ receptor agonists which interact more favourably with the α2 and/or α3 subunit than with α1 will be effective in the treatment of anxiety with a reduced propensity to cause sedation. Moreover, agents which are inverse agonists of the α5 subunit are likely to be beneficial in enhancing cognition, for example in subjects suffering from dementing conditions such as Alzheimer's disease. Also, agents which are antagonists or inverse agonists at α1 might be employed to reverse sedation or hypnosis caused by α1 agonists.

The compounds of the present invention, being selective ligands for $GABA_A$ receptors, are therefore of use in the treatment and/or prevention of a variety of disorders of the central nervous system. Such disorders include anxiety disorders, such as panic disorder with or without agoraphobia, agoraphobia without history of panic disorder, animal and other phobias including social phobias, obsessive-compulsive disorder, stress disorders including post-traumatic and acute stress disorder, and generalized or substance-induced anxiety disorder; neuroses; convulsions; migraine; depressive or bipolar disorders, for example single-episode or recurrent major depressive disorder, dysthymic disorder, bipolar I and bipolar II manic disorders, and cyclothymic disorder; psychotic disorders including schizophrenia; neurodegeneration arising from cerebral ischemia; attention deficit hyperactivity disorder; Tourette's syndrome; speech disorders, including stuttering; and disorders of circadian rhythm, e.g. in subjects suffering from the effects of jet lag or shift work.

Further disorders for which selective ligands for $GABA_A$ receptors may be of benefit include pain and nociception; emesis, including acute, delayed and anticipatory emesis, in particular emesis induced by chemotherapy or radiation, as well as motion sickness, and post-operative nausea and vomiting; eating disorders including anorexia nervosa and bulimia nervosa; premenstrual syndrome; muscle spasm or spasticity, e.g. in paraplegic patients; hearing disorders, including tinnitus and age-related hearing impairment; urinary incontinence; and the effects of substance abuse or dependency, including alcohol withdrawal. Selective ligands for $GABA_A$ receptors may be beneficial in enhancing cognition, for example in subjects suffering from dementing conditions such as Alzheimer's disease; and may also be effective as pre-medication prior to anaesthesia or minor procedures such as endoscopy, including gastric endoscopy.

In addition, the compounds in accordance with the present invention may be useful as radioligands in assays for detecting compounds capable of binding to the human $GABA_A$ receptor.

The present invention provides a class of imidazotriazinone derivatives which possess desirable binding properties at various $GABA_A$ receptor subtypes. The compounds in accordance with the present invention have good affinity as ligands for the α2 and/or α3 and/or α5 subunit of the human $GABA_A$ receptor. The compounds of this invention may interact more favourably with the α2 and/or α3 subunit than with the α1 subunit; and/or may interact more favourably with the α5 subunit than with the α1 subunit.

The compounds of the present invention are $GABA_A$ receptor subtype ligands having a binding affinity ($K_i$) for the α2 and/or α3 and/or α5 subunit, as measured in the assay described hereinbelow, of 200 nM or less, typically of 100 nM or less, and ideally of 20 nM or less. The compounds in accordance with this invention may possess at least a 2-fold, suitably at least a 5-fold, and advantageously at least a 10-fold, selective affinity for the α2 and/or α3 and/or α5 subunit relative to the α1 subunit. However, compounds which are not selective in terms of their binding affinity for the α2 and/or α3 and/or α5 subunit relative to the α1 subunit are also encompassed within the scope of the present invention; such compounds will desirably exhibit functional selectivity in terms of zero or weak (positive or negative) efficacy at the α1 subunit and (i) a full or partial agonist profile at the α2 and/or α3 subunit, and/or (ii) an inverse agonist profile at the α5 subunit.

The present invention provides a compound of formula I, or a pharmaceutically acceptable salt thereof:

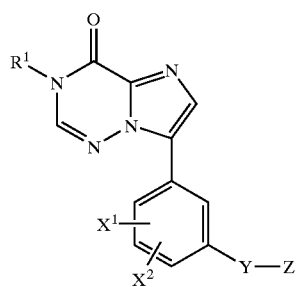

(I)

wherein $X^1$ represents hydrogen, halogen, $C_{1-6}$ alkyl, trifluoromethyl or $C_{1-6}$ alkoxy;

$X^2$ represents hydrogen or halogen;

Y represents a chemical bond, an oxygen atom, or a —NH— linkage;

Z represents an optionally substituted aryl or heteroaryl group;

$R^1$ represents hydrocarbon, a heterocyclic group, trifluoromethyl, —$SO_2R^a$, —$SO_2NR^aR^b$, —$COR^a$, —$CO_2R^a$ or —$CONR^aR^b$; and $R^a$ and $R^b$ independently represent hydrogen, hydrocarbon or a heterocyclic group.

The aryl or heteroaryl group Z in the compounds of formula I above may be unsubstituted, or substituted by one or more substituents. Typically, the group Z will be unsubstituted, or substituted by one or two substituents. Suitably, the group Z is unsubstituted or monosubstituted. Typical substituents on the group Z include halogen, cyano, nitro, $C_{1-6}$ alkyl, hydroxy, $C_{1-6}$ alkoxy, oxy, $C_{1-6}$ alkylsulphonyl, amino, aminocarbonyl, formyl, $C_{2-6}$ alkoxycarbonyl and —$CR^a$=$NOR^b$, wherein $R^a$ and $R^b$ are as defined above.

For use in medicine, the salts of the compounds of formula I will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The term "hydrocarbon" as used herein includes straight-chained, branched and cyclic groups containing up to 18 carbon atoms, suitably up to 15 carbon atoms, and conveniently up to 12 carbon atoms. Suitable hydrocarbon groups include $C_{1-6}$ alkyl, $C_{2-6}$ alkenyl, $C_{2-6}$ alkynyl, $C_{3-7}$ cycloalkyl, $C_{3-7}$ cycloalkyl($C_{1-6}$)alkyl, indanyl, aryl and aryl($C_{1-6}$)alkyl.

The expression "a heterocyclic group" as used herein includes cyclic groups containing up to 18 carbon atoms and at least one heteroatom preferably selected from oxygen, nitrogen and sulphur. The heterocyclic group suitably contains up to 15 carbon atoms and conveniently up to 12 carbon atoms, and is preferably linked through carbon. Examples of suitable heterocyclic groups include $C_{3-7}$ heterocycloalkyl, $C_{3-7}$ heterocycloalkyl($C_{1-6}$)alkyl, heteroaryl and heteroaryl($C_{1-6}$)alkyl groups.

Suitable alkyl groups include straight-chained and branched alkyl groups containing from 1 to 6 carbon atoms. Typical examples include methyl and ethyl groups, and straight-chained or branched propyl, butyl and pentyl groups. Particular alkyl groups are methyl, ethyl, n-propyl, isopropyl, isobutyl, tert-butyl and 2,2-dimethylpropyl. Derived expressions such as "$C_{1-6}$ alkoxy", "$C_{1-6}$ alkylamino" and "$C_{1-6}$ alkylsulphonyl" are to be construed accordingly.

Suitable alkenyl groups include straight-chained and branched alkenyl groups containing from 2 to 6 carbon atoms. Typical examples include vinyl, allyl and dimethylallyl groups.

Suitable alkynyl groups include straight-chained and branched alkynyl groups containing from 2 to 6 carbon atoms. Typical examples include ethynyl and propargyl groups.

Suitable cycloalkyl groups include groups containing from 3 to 7 carbon atoms. Particular cycloalkyl groups are cyclopropyl and cyclohexyl.

Typical examples of $C_{3-7}$ cycloalkyl($C_{1-6}$)alkyl groups include cyclopropylmethyl, cyclohexylmethyl and cyclohexylethyl.

Particular indanyl groups include indan-1-yl and indan-2-yl.

Particular aryl groups include phenyl and naphthyl, preferably phenyl.

Particular aryl($C_{1-6}$)alkyl groups include benzyl, phenylethyl, phenylpropyl and naphthylmethyl.

Suitable heterocycloalkyl groups include azetidinyl, pyrrolidinyl, piperidinyl, piperazinyl, morpholinyl and thiomorpholinyl groups.

Suitable heteroaryl groups include pyridinyl, quinolinyl, isoquinolinyl, pyridazinyl, pyrimidinyl, pyrazinyl, furyl, benzofuryl, dibenzofuryl, thienyl, benzthienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl and tetrazolyl groups.

The expression "heteroaryl($C_{1-6}$)alkyl" as used herein includes furylmethyl, furylethyl, thienylmethyl, thienylethyl, oxazolylmethyl, oxazolylethyl, thiazolylmethyl, thiazolylethyl, imidazolylmethyl, imidazolylethyl, oxadiazolylmethyl, oxadiazolylethyl, thiadiazolylmethyl, thiadiazolylethyl, triazolylmethyl, triazolylethyl, tetrazolylmethyl, tetrazolylethyl, pyridinylmethyl, pyridinylethyl, pyrimidinylmethyl, pyrazinylmethyl, quinolinylmethyl and isoquinolinylmethyl.

The hydrocarbon and heterocyclic groups may in turn be optionally substituted by one or more groups selected from $C_{1-6}$ alkyl, adamantyl, phenyl, halogen, $C_{1-6}$ haloalkyl, $C_{1-6}$ aminoalkyl, trifluoromethyl, hydroxy, $C_{1-6}$ alkoxy, aryloxy, keto, $C_{1-3}$ alkylenedioxy, nitro, cyano, carboxy, $C_{2-6}$ alkoxycarbonyl, $C_{2-6}$ alkoxycarbonyl($C_{1-6}$)alkyl, $C_{2-6}$ alkylcarbonyloxy, arylcarbonyloxy, aminocarbonyloxy, $C_{2-6}$ alkylcarbonyl, arylcarbonyl, $C_{1-6}$ alkylthio, $C_{1-6}$ alkylsulphinyl, $C_{1-6}$ alkylsulphonyl, arylsulphonyl, —NR$^v$R$^w$, —NR$^v$COR$^w$, —NR$^v$CO$_2$R$^w$, —NR$^v$SO$_2$R$^w$, —CH$_2$NR$^v$SO$_2$R$^w$, —NHCONR$^v$R$^w$, —CONR$^v$R$^w$, —SO$_2$NR$^v$R$^w$ and —CH$_2$SO$_2$NR$^v$R$^w$, in which R$^v$ and R$^w$ independently represent hydrogen, $C_{1-6}$ alkyl, aryl or aryl($C_{1-6}$)alkyl.

The term "halogen" as used herein includes fluorine, chlorine, bromine and iodine, especially fluoro or chloro.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof in any proportion are encompassed within the scope of the present invention.

Suitable values for the $X^1$ substituent include hydrogen, fluoro, chloro, methyl, trifluoromethyl and methoxy; in particular hydrogen or fluoro; and especially fluoro.

Typical values of $X^2$ include hydrogen and fluoro, especially hydrogen.

In a preferred embodiment, Y represents a chemical bond.
In another embodiment, Y represents an oxygen atom.
In a further embodiment, Y represents a —NH— linkage.

Selected values for the substituent Z include phenyl, pyridinyl, pyridazinyl, pyrimidinyl, pyrazinyl, furyl, thienyl, oxazolyl, isoxazolyl, thiazolyl, isothiazolyl, pyrrolyl, pyrazolyl, imidazolyl, oxadiazolyl, thiadiazolyl, triazolyl and tetrazolyl, any of which groups may be optionally substituted by one or more substituents.

In one favoured embodiment, Z represents an optionally substituted phenyl group, in particular monosubstituted or disubstituted phenyl. In another favoured embodiment, Z represents optionally substituted pyridinyl, especially unsubstituted, monosubstituted or disubstituted pyridin-2-yl, pyridin-3-yl or pyridin-4-yl.

Examples of suitable substituents on the group Z include fluoro, chloro, cyano, nitro, methyl, hydroxy, methoxy, oxy, methanesulphonyl, amino, aminocarbonyl, formyl, methoxycarbonyl and —CH═NOH.

Examples of particular substituents on the group Z include fluoro and cyano, especially cyano.

Detailed values of Z include cyanophenyl, (cyano)(fluoro)phenyl, (chloro)(cyano)phenyl, nitrophenyl, methoxyphenyl, methanesulphonyl-phenyl, pyridinyl, fluoro-pyridinyl, difluoro-pyridinyl, (amino)(chloro)pyridinyl, cyano-pyridinyl, methyl-pyridinyl, hydroxy-pyridinyl, methoxy-pyridinyl, oxy-pyridinyl, aminocarbonyl-pyridinyl, pyridazinyl, pyrimidinyl, pyrazinyl, cyano-thienyl, aminocarbonyl-thienyl, formyl-thienyl, methoxycarbonyl-thienyl, thienyl-CH═NOH, thiazolyl, isothiazolyl, pyrrolyl, pyrazolyl, imidazolyl, triazolyl and methyl-tetrazolyl.

Specific values of Z include cyanophenyl, (cyano)(fluoro)phenyl, pyridinyl, difluoro-pyridinyl and cyano-pyridinyl.

In one embodiment, Z represents (cyano)(fluoro)phenyl, especially 2-cyano-4-fluorophenyl.

Typically, $R^1$ represents hydrocarbon, a heterocyclic group, trifluoromethyl, —COR$^a$ or —CO$_2$R$^a$.

Typical values of R$^a$ include hydrogen and $C_{1-6}$ alkyl. Suitably, R$^a$ represents hydrogen or methyl.

Typical values of R$^b$ include hydrogen, $C_{1-6}$ alkyl, hydroxy($C_{1-6}$)alkyl and di($C_{1-6}$)alkylamino($C_{1-6}$)alkyl. Suitably, R$^b$ represents hydrogen, methyl, ethyl, hydroxyethyl or dimethylaminoethyl. Particular values of R$^b$ include hydrogen, hydroxyethyl and dimethylaminoethyl, especially hydrogen or dimethylaminoethyl.

Suitable values of $R^1$ include $C_{1-6}$ alkyl, halo($C_{1-6}$)alkyl, dihalo($C_{1-6}$)alkyl, hydroxy($C_{1-6}$)alkyl, dihydroxy($C_{1-6}$)alkyl, $C_{1-6}$ alkoxy($C_{1-6}$)alkyl, di($C_{1-6}$)alkoxy($C_{1-6}$)alkyl, cyano($C_{1-6}$)alkyl, $C_{2-6}$ alkoxycarbonyl($C_{1-6}$)alkyl, $C_{3-7}$ cycloalkyl, heteroaryl, $C_{1-6}$ alkyl-heteroaryl, heteroaryl($C_{1-6}$) alkyl, trifluoromethyl, formyl, $C_{2-6}$ alkylcarbonyl and $C_{2-6}$ alkoxycarbonyl.

Representative values of $R^1$ include $C_{1-6}$ alkyl, halo($C_{1-6}$)alkyl, dihalo($C_{1-6}$)alkyl, hydroxy($C_{1-6}$)alkyl and trifluoromethyl.

Individual values of $R^1$ include methyl, ethyl, fluoromethyl, difluoromethyl, methoxymethyl, dimethoxymethyl, hydroxyethyl (especially 2-hydroxyethyl), fluoroethyl (especially 2-fluoroethyl), difluoroethyl (especially 2,2-difluoroethyl), dimethoxyethyl (especially 2,2-dimethoxyethyl), isopropyl, hydroxypropyl, dihydroxypropyl (especially 1,2-dihydroxyprop-2-yl), cyanopropyl, methoxycarbonylpropyl (especially 2-methoxycarbonylprop-2-yl), tert-butyl, hydroxybutyl (especially 1-hydroxy-2-methylprop-2-yl), cyclopropyl, pyridinyl, furyl, thienyl, oxazolyl, methylthiazolyl, methyloxadiazolyl, imidazolylmethyl, triazolylmethyl, trifluoromethyl, formyl, acetyl and methoxycarbonyl.

In a first embodiment, $R^1$ represents methyl. In a second embodiment, $R^1$ represents ethyl. In a third embodiment, $R^1$ represents fluoroethyl (especially 2-fluoroethyl). In a fourth embodiment, $R^1$ represents difluoroethyl (especially 2,2-difluoroethyl). In an additional embodiment, $R^1$ represents trifluoromethyl.

A particular sub-class of compounds according to the invention is represented by the compounds of formula IIA, and pharmaceutically acceptable salts thereof:

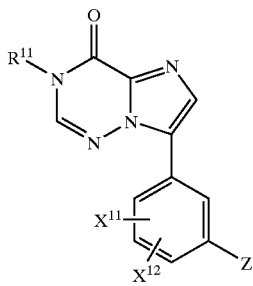

(IIA)

wherein

Z is as defined above;

$X^{11}$ represents hydrogen, fluoro, chloro, methyl, trifluoromethyl or methoxy;

$X^{12}$ represents hydrogen or fluoro; and $R^{11}$ represents $C_{1-6}$ alkyl, halo($C_{1-6}$)alkyl, dihalo($C_{1-6}$)alkyl, hydroxy($C_{1-6}$)alkyl, dihydroxy($C_{1-6}$)alkyl, $C_{1-6}$ alkoxy($C_{1-6}$)alkyl, di($C_{1-6}$)alkoxy($C_{1-6}$)alkyl, cyano($C_{1-6}$)alkyl, $C_{2-6}$ alkoxycarbonyl($C_{1-6}$)alkyl, $C_{3-7}$ cycloalkyl, heteroaryl, $C_{1-6}$ alkyl-heteroaryl, heteroaryl($C_{1-6}$)alkyl, trifluoromethyl, formyl, $C_{2-6}$ alkylcarbonyl or $C_{2-6}$ alkoxycarbonyl.

Suitable values of $X^{11}$ include hydrogen and fluoro, especially fluoro.

In a favoured embodiment, $X^{12}$ represents hydrogen. In another embodiment, $X^{12}$ represents fluoro.

Where $R^{11}$ represents heteroaryl, this group is suitably pyridinyl, furyl, thienyl or oxazolyl.

Where $R^{11}$ represents $C_{1-6}$ alkyl-heteroaryl, this group is suitably methylthiazolyl (e.g. 2-methylthiazol-5-yl) or methyloxadiazolyl (e.g. 3-methyl-[1,2,4]oxadiazol-5-yl).

Where $R^{11}$ represents heteroaryl($C_{1-6}$)alkyl, this group is suitably imidazolylmethyl or triazolylmethyl.

Representative values of $R^{11}$ include $C_{1-6}$ alkyl, halo($C_{1-6}$)alkyl, dihalo($C_{1-6}$)alkyl, hydroxy($C_{1-6}$)alkyl and trifluoromethyl.

Individual values of $R^{11}$ include methyl, ethyl, fluoromethyl, difluoromethyl, methoxymethyl, dimethoxymethyl, hydroxyethyl (especially 2-hydroxyethyl), fluoroethyl (especially 2-fluoroethyl), difluoroethyl (especially 2,2-difluoroethyl), dimethoxyethyl (especially 2,2-dimethoxyethyl), isopropyl, hydroxypropyl, dihydroxypropyl (especially 1,2-dihydroxyprop-2-yl), cyanopropyl, methoxycarbonylpropyl (especially 2-methoxycarbonylprop-2-yl), tert-butyl, hydroxybutyl (especially 1-hydroxy-2-methylprop-2-yl), cyclopropyl, pyridinyl, furyl, thienyl, oxazolyl, methylthiazolyl, methyloxadiazolyl, imidazolylmethyl, triazolylmethyl, trifluoromethyl, formyl, acetyl and methoxycarbonyl.

In a first embodiment, $R^{11}$ represents methyl. In a second embodiment, $R^{11}$ represents ethyl. In a third embodiment, $R^{11}$ represents fluoroethyl (especially 2-fluoroethyl). In a fourth embodiment, $R^{11}$ represents difluoroethyl (especially 2,2-difluoroethyl). In an additional embodiment, $R^{11}$ represents trifluoromethyl.

One representative subset of the compounds of formula IIA above is represented by the compounds of formula IIB, and pharmaceutically acceptable salts thereof:

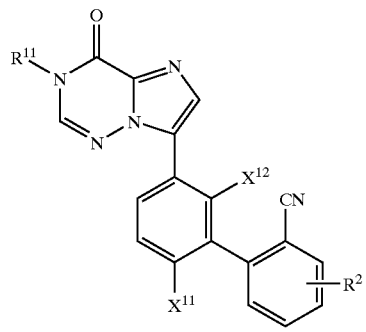

(IIB)

wherein $X^{11}$, $X^{12}$ and $R^{11}$ are as defined above; and $R^2$ represents hydrogen or fluoro.

In one embodiment, $R^2$ is hydrogen.

In another embodiment, $R^2$ is fluoro, in which case the fluorine atom $R^2$ is favourably attached to the phenyl ring at the 4-, 5- or 6-position (relative to the cyano group at position 2).

Another representative subset of the compounds of formula IIA above is represented by the compounds of formula IIC, and pharmaceutically acceptable salts thereof:

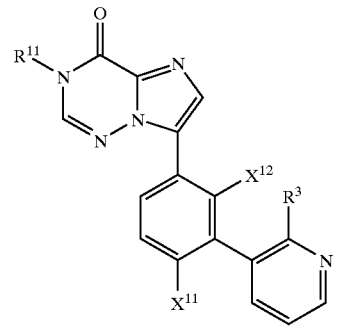

(IIC)

wherein $X^{11}$, $X^{12}$ and $R^{11}$ are as defined above; and $R^3$ represents hydrogen, fluoro, cyano or methyl.

In one embodiment, $R^3$ is hydrogen.

In an additional embodiment, $R^3$ is fluoro.

In another embodiment, $R^3$ is cyano.

In a further embodiment, $R^3$ is methyl.

A further representative subset of the compounds of formula IIA above is represented by the compounds of formula IID, and pharmaceutically acceptable salts thereof:

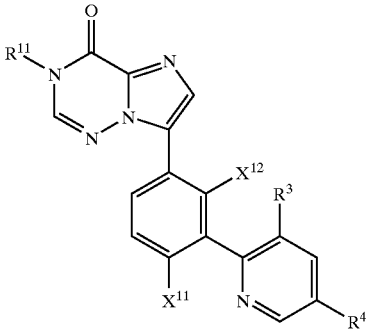

(IID)

wherein $X^{11}$, $X^{12}$, $R^3$ and $R^{11}$ are as defined above; and
$R^4$ represents hydrogen or fluoro.
Suitably, $R^4$ represents hydrogen.
In another embodiment, $R^4$ represents fluoro.
Specific compounds within the scope of the present invention include:
4,2'-difluoro-5'-(3-methyl-4-oxo-3,4-dihydroimidazo[2,1-f][1,2,4]triazin-7-yl)biphenyl-2-carbonitrile;
and pharmaceutically acceptable salts thereof.

Also provided by the present invention is a method for the treatment and/or prevention of anxiety which comprises administering to a patient in need of such treatment an effective amount of a compound of formula I as defined above or a pharmaceutically acceptable salt thereof.

Further provided by the present invention is a method for the treatment and/or prevention of convulsions (e.g. in a patient suffering from epilepsy or a related disorder) which comprises administering to a patient in need of such treatment an effective amount of a compound of formula I as defined above or a pharmaceutically acceptable salt thereof. The binding affinity ($K_i$) of the compounds according to the present invention for the α3 subunit of the human $GABA_A$ receptor is conveniently as measured in the assay described hereinbelow. The α3 subunit binding affinity ($K_i$) of the anxiolytic compounds of the invention is ideally 50 nM or less, preferably 10 nM or less, and more preferably 5 nM or less.

The anxiolytic compounds according to the present invention will ideally elicit at least a 40%, preferably at least a 50%, and more preferably at least a 60%, potentiation of the GABA $EC_{20}$ response in stably transfected recombinant cell lines expressing the α3 subunit of the human $GABA_A$ receptor. Moreover, the compounds of the invention will ideally elicit at most a 30%, preferably at most a 20%, and more preferably at most a 10%, potentiation of the GABA $EC_{20}$ response in stably transfected recombinant cell lines expressing the al subunit of the human $GABA_A$ receptor.

The potentiation of the GABA $EC_{20}$ response in stably transfected cell lines expressing the α3 and α1 subunits of the human $GABA_A$ receptor can conveniently be measured by procedures analogous to the protocol described in Wafford et al., *Mol. Pharmacol.*, 1996, 50, 670–678. The procedure will suitably be carried out utilising cultures of stably transfected eukaryotic cells, typically of stably transfected mouse Ltk⁻ fibroblast cells.

The compounds according to the present invention may exhibit anxiolytic activity, as may be demonstrated by a positive response in the elevated plus maze and conditioned suppression of drinking tests (cf. Dawson et al., *Psychopharmacology*, 1995, 121, 109–117). Moreover, the compounds of the invention are likely to be substantially non-sedating, as may be confirmed by an appropriate result obtained from the response sensitivity (chain-pulling) test (cf. Bayley et al., *J. Psychopharmacol.*, 1996, 10, 206–213).

The compounds according to the present invention may also exhibit anticonvulsant activity. This can be demonstrated by the ability to block pentylenetetrazole-induced seizures in rats and mice, following a protocol analogous to that described by Bristow et al. in *J. Pharmacol. Exp. Ther.*, 1996, 279, 492–501.

In another aspect, the present invention provides a method for the treatment and/or prevention of cognitive disorders, including dementing conditions such as Alzheimer's disease, which comprises administering to a patient in need of such treatment an effective amount of a compound of formula I as defined above or a pharmaceutically acceptable salt thereof.

Cognition enhancement can be shown by testing the compounds in the Morris watermaze as reported by McNamara and Skelton, *Psychobiology*, 1993, 21, 101–108. Further details of relevant methodology are described in WO 96/25948.

Cognitive disorders for which the compounds of the present invention may be of benefit include delirium, dementia, amnestic disorders, and cognition deficits, including age-related memory deficits, due to traumatic injury, stroke, Parkinson's disease and Down Syndrome. Any of these conditions may be attributable to substance abuse or withdrawal. Examples of dementia include dementia of the Alzheimer's type with early or late onset, and vascular dementia, any of which may be uncomplicated or accompanied by delirium, delusions or depressed mood; and dementia due to HIV disease, head trauma, Parkinson's disease or Creutzfeld-Jakob disease.

In order to elicit their behavioural effects, the compounds of the invention will ideally be brain-penetrant; in other words, these compounds will be capable of crossing the so-called "blood-brain barrier". Preferably, the compounds of the invention will be capable of exerting their beneficial therapeutic action following administration by the oral route.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

In the treatment of neurological disorders, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The compounds in accordance with the present invention may be prepared by a process which comprises reacting a compound of formula III with a compound of formula IV:

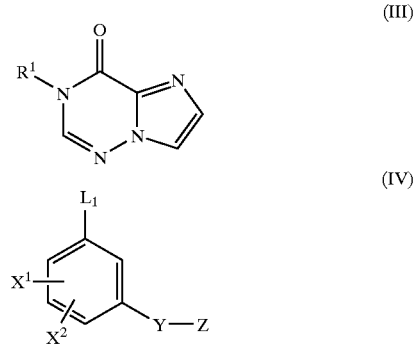

wherein $X^1$, $X^2$, Y, Z and $R^1$ are as defined above, and $L^1$ represents a suitable leaving group; in the presence of a transition metal catalyst.

The leaving group $L^1$ is typically a halogen atom, e.g. bromo.

The transition metal catalyst of use in the reaction between compounds III and IV is suitably palladium(II) acetate, in which case the reaction is typically accomplished in the presence of triphenylphosphine. The reaction is conveniently carried out at an elevated temperature in a solvent such as N,N-dimethylacetamide, typically in the presence of potassium acetate.

The intermediates of formula III may suitably be prepared by the method described in the accompanying Example, or by procedures analogous thereto.

The intermediates of formula IV may be prepared by the procedures described in WO 02/38568, or by alternative procedures known from the art.

It will be understood that any compound of formula I initially obtained from any of the above processes may, where appropriate, subsequently be elaborated into a further compound of formula I by techniques known from the art. For example, a compound of formula I wherein $R^1$ represents —C(O-Alk$^1$)$_2$R$^a$ initially obtained, wherein Alk$^1$ is $C_{1-6}$ alkyl, typically methyl or ethyl, may be converted into the corresponding compound of formula I wherein $R^1$ represents —COR$^a$ by hydrolysis with a mineral acid, typically aqueous hydrochloric acid. A compound of formula I wherein $R^1$ represents —COR$^a$ may be converted into the corresponding compound of formula I wherein $R^1$ represents —CF$_2$R$^a$ by treatment with (diethylamino)sulfur trifluoride (DAST). A compound of formula I wherein $R^1$ represents —COCH$_3$ may be treated with thioacetamide in the presence of pyridinium tribromide to furnish the corresponding compound of formula I wherein $R^1$ represents 2-methylthiazol-5-yl. Moreover, a compound of formula I wherein $R^1$ is formyl may be treated with (P-tolylsulfonyl) methyl isocyanide (TosMIC) in the presence of potassium carbonate to afford the corresponding compound of formula I wherein $R^1$ represents oxazol-5-yl. A compound of formula I wherein Z is substituted with methoxy may be converted to the corresponding compound wherein Z is substituted with hydroxy by treatment with boron tribromide.

Where a mixture of products is obtained from any of the processes described above for the preparation of compounds according to the invention, the desired product can be separated therefrom at an appropriate stage by conventional methods such as preparative HPLC; or column chromatography utilising, for example, silica and/or alumina in conjunction with an appropriate solvent system.

Where the above-described processes for the preparation of the compounds according to the invention give rise to mixtures of stereoisomers, these isomers may be separated by conventional techniques such as preparative chromatography. The novel compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-1-tartaric acid, followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 3rd edition, 1999. The protecting groups may be removed at a convenient subsequent stage using methods known from the art.

The following Example illustrates the preparation of compounds according to the invention.

The compounds in accordance with this invention potently inhibit the binding of [$^3$H]-flumazenil to the benzodiazepine binding site of human GABA$_A$ receptors containing the α2 and/or α3 and/or α5 subunit stably expressed in Ltk$^−$ cells.

Reagents

Phosphate buffered saline (PBS).

Assay buffer: 10 mM KH$_2$PO$_4$, 100 mM KCl, pH 7.4 at room temperature.

[$^3$H]-Flumazenil (18 nM for α1β3γ2 cells; 18 nM for α2β3γ2 cells; 10 nM for α3β3γ2 cells; 10 nM for α5β3γ2 cells) in assay buffer.

Flunitrazepam 100 μM in assay buffer.

Cells resuspended in assay buffer (1 tray to 10 ml).

Harvesting Cells

Supernatant is removed from cells. PBS (approximately 20 ml) is added. The cells are scraped and placed in a 50 ml centrifuge tube. The procedure is repeated with a further 10 ml of PBS to ensure that most of the cells are removed. The cells are pelleted by centrifuging for 20 min at 3000 rpm in a benchtop centrifuge, and then frozen if desired. The pellets are resuspended in 10 ml of buffer per tray (25 cm×25 cm) of cells.

Assay

Can be carried out in deep 96-well plates or in tubes. Each tube contains:

300 μl of assay buffer.

50 μl of [³H]-flumazenil (final concentration for α1β3γ2:1.8 nM; for α2β3γ2:1.8 nM; for α3β3γ2:1.0 nM; for α5β3γ2:1.0 nM).

0.50 μl of buffer or solvent carrier (e.g. 10% DMSO) if compounds are dissolved in 10% DMSO (total); test compound or flunitrazepam (to determine non-specific binding), 10 μM final concentration.

100 μl of cells.

Assays are incubated for 1 hour at 40° C., then filtered using either a Tomtec or Brandel cell harvester onto GF/B filters followed by 3×3 ml washes with ice cold assay buffer. Filters are dried and counted by liquid scintillation counting. Expected values for total binding are 3000–4000 dpm for total counts and less than 200 dpm for non-specific binding if using liquid scintillation counting, or 1500–2000 dpm for total counts and less than 200 dpm for non-specific binding if counting with meltilex solid scintillant. Binding parameters are determined by non-linear least squares regression analysis, from which the inhibition constant $K_i$ can be calculated for each test compound.

The compound of the accompanying Example was tested in the above assay, and was found to possess a $K_i$ value for displacement of [³H]-flumazenil from the α2 and/or α3 and/or α5 subunit of the human GABAA receptor of 100 nM or less.

EXAMPLE 1

4,2'-Difluoro-5'-(3-methyl-4-oxo-3,4-dihydroimidazo[2,1-f][1,2,4]triazin-7-yl)biphenyl-2-carbonitrile A suspension of 4-methyl-3-thiosemicarbazide (10.0 g, 95 mmol) in ethanol (60 ml) was heated to 60° C. and the resulting suspension treated with methyl iodide (13.5 g, 95 mmol). The reaction was stirred for 20 min then allowed to cool to ambient temperature. The resulting solid was filtered, washed with ethanol (30 ml) and diethyl ether (20 ml) and left to air dry which gave 4-methyl-3-methylthiosemicarbazide hydroiodide (1:1 mixture of E and Z isomers) (18.52 g, 79%) as a white solid: $\delta_H$ (360 MHz, DMSO) 2.43 (3H, s), 2.59 (3H, s), 2.87 (3H, s), 2.93 (3H, s).

4-Methyl-3-methylthiosemicarbazide hydroiodide (7.41 g, 30 mmol), ethyl thiooxamate (4.0 g, 30 mmol) and triethylamine (3.0 g, 30 mmol) were dissolved in ethanol (150 ml) and heated under reflux for 2 h. The mixture was allowed to cool and aged at room temperature for 66 h. The resulting solid was filtered, washed with ethanol (10 ml) and left to air-dry which gave 6-amino-4-methyl-3-methylsulfanyl-4H-[1,2,4]triazin-5-one (1.50 g, 29%) as a yellow solid: $\delta_H$ (400 MHz, DMSO) 2.51 (3H, s), 3.37 (3H, s), 6.56 (2H, s).

Bromoacetaldehyde dimethyl acetal (2.57 g, 13.1 mmol), 48% hydrobromic acid (1.06 g, 13.1 mmol) and water (1.5 ml) were heated at 95° C. for 1.5 h. The mixture was allowed to cool to ambient temperature, diluted with propan-2-ol (20 ml) then treated with sodium hydrogen-carbonate (1.46 g, 17.4 mmol) added in portions over 5 min. The mixture was filtered and the filtrate was added to 6-amino-4-methyl-3-methylsulfanyl-4H-[1,2,4]triazin-5-one (1.50 g, 8.71 mmol). The resulting suspension was heated at 95° C. for 18 h. The mixture was allowed to cool to ambient temperature, diluted with methanol (100 ml) and evaporated onto silica. The product was purified by flash column chromatography on silica eluting with dichloromethane (+0.1% 0.880 ammonia) on a gradient of methanol (3–6%). Collecting appropriate fractions gave 3-methyl-2-methylsulfanyl-3H-imidazo[2,1-f][1,2,4]triazin-4-one (0.81 g, 47%) as a pale yellow solid: $\delta_H$ (400 MHz, CDCl₃) 2.61 (3H, s), 3.58 (3H, s), 7.49 (1H, d, J1), 7.52 (1H, d, J1).

3-Methyl-2-methylsulfanyl-3H-imidazo[2,1-f][1,2,4]triazin-4-one (0.81 g, 4.1 mmol) was suspended in ethanol (10 ml) and the mixture heated to 40° C. 6×1 ml pipette amounts of Raney-nickel (50 micron stored in water) were added in portions over 9 h. On complete addition the mixture was heated at 40° C. for a further 9 h. The mixture was allowed to cool to ambient temperature and the mixture filtered through Celite. The filtrate was evaporated and the residue purified by flash column chromatography on silica eluting with 2% methanol in dichloromethane. Collecting appropriate fractions gave 3-methyl-3H-imidazo[2,1-f][1,2,4]triazin-4-one (150 mg, 24%) as an off-white solid: $\delta_H$ (400 MHz, CDCl₃) 3.59 (3H, s), 7.55 (1H, d, J1), 7.60 (1H, d, J1), 7.73 (1H, s).

3-Methyl-3H-imidazo[2,1-f][1,2,4]triazin-4-one (75 mg, 0.5 mmol), 5'-bromo-4,2'-difluorobiphenyl-2-carbonitrile (prepared according to the procedure described in WO 02/38568) (220 mg, 0.75 mmol) and potassium acetate (74 mg, 0.75 mmol) were suspended in N,N-dimethylacetamide (2 ml) and degassed with nitrogen for 10 min. Palladium(II) acetate (5.6 mg, 0.025 mmol) and triphenylphosphine (6.6 mg, 0.025 mmol) were added and the mixture heated at 120° C. for 1 h. The mixture was allowed to cool to ambient temperature, diluted with ethyl acetate (100 ml), washed with water (50 ml) and brine (30 ml), dried over anhydrous sodium sulfate, filtered and evaporated to give a brown solid. The solid was purified by flash column chromatography on silica, eluting with dichloromethane on a gradient of methanol (0–2%). The appropriate fractions were collected and concentrated, and the residue triturated with diethyl ether, which gave 4,2'-difluoro-5'-(3-methyl-4-oxo-3,4-dihydroimidazo[2,1-f][1,2,4] triazin-7-yl)biphenyl-2-carbonitrile (139 mg, 77%) as a white solid: $\delta_H$ (500 MHz, CDCl₃) 3.55 (3H, s), 7.27 (1H, dd, J9 and 9), 7.35 (1H, ddd, J8, 8 and 3), 7.45 (1H, dd, J8 and 3), 7.47–7.49 (1H, m), 7.71 (1H, s), 7.73 (1H, s), 7.89–7.92 (2H, m); m/z (ES⁺) 364 (M⁺+H).

What is claimed is:

1. A compound of formula I, or a pharmaceutically acceptable salt thereof:

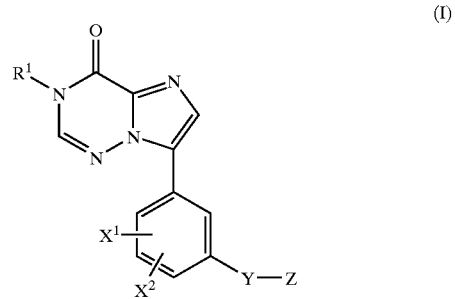

(I)

wherein:

$X^1$ represents hydrogen, halogen, $C_{1-6}$ alkyl, trifluoromethyl or $C_{1-6}$ alkoxy;

$X^2$ represents hydrogen or halogen;

Y represents a chemical bond, an oxygen atom, or a —NH— linkage;

Z represents a phenyl, pyridinyl, quinolinyl, isoquinolinyl, pyridazinyl, pyrimidinyl, pyrazinyl, furyl, benzofuryl, dibenzofuryl, thienyl, benzthienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl or tetrazolyl group, which group is unsubstituted or substituted with one or more substituents selected from: halogen, cyano, nitro, $C_{1-6}$ alkyl, hydroxy, $C_{1-6}$ alkoxy, oxy, $C_{1-6}$ alkylsulphonyl, amino, aminocarbonyl, formyl, $C_{2-6}$ alkoxycarbonyl and —$CR^a$=$NOR^b$;

$R^1$ represents a group selected from: $C_{1-6}$ alkyl, $C_{2-6}$ alkenyl, $C_{2-6}$ alkynyl, $C_{3-7}$ cycloalkyl, $C_{3-7}$ cycloalkyl($C_{1-6}$ alkyl), indanyl, phenyl, phenyl($C_{1-6}$ alkyl), azetidinyl, pyrrolidinyl, piperidinyl, piperazinyl, morpholinyl, thiomorpholinyl, pyridinyl, quinolinyl, isoquinolinyl, pyridazinyl, pyrimidinyl, pyrazinyl, furyl, benzofuryl, dibenzofuryl, thienyl, benzthienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl and tetrazolyl, which group is unsubstituted or substituted with one or more substituents selected from:

$C_{1-6}$ alkyl, adamantyl, phenyl, halogen, $C_{1-6}$ haloalkyl, $C_{1-6}$ aminoalkyl, trifluoromethyl, hydroxy, $C_{1-6}$ alkoxy, aryloxy, keto, $C_{1-3}$ alkylenedioxy, nitro, cyano, carboxy, $C_{2-6}$ alkoxycarbonyl, $C_{2-6}$ alkoxycarbonyl($C_{1-6}$)alkyl, $C_{2-6}$ alkylcarbonyloxy, arylcarbonyloxy, aminocarbonyloxy, $C_{2-6}$ alkylcarbonyl, arylcarbonyl, $C_{1-6}$ alkylthio, $C_{1-6}$ alkylsulphinyl, $C_{1-6}$ alkylsulphonyl, phenylsulphonyl, —$NR^vR^w$, —$NR^vCOR^w$, —$NR^vCO_2R^w$, —$NR^vSO_2R^w$, —$CH_2NR^vSO_2R^w$, —$NHCONR^vR^w$, —$CONR^vR^w$, —$SO_2NR^vR^w$ and —$CH_2SO_2NR^vR^w$, in which $R^v$ and $R^w$ independently represent hydrogen $C_{1-6}$ alkyl, phenyl or phenyl($C_{1-6}$)alkyl, or $R^1$ represents a group selected from: trifluoromethyl, —$SO_2R^a$, —$SO_2NR^aR^b$, —$COR^a$, —$CO_2R^a$ and —$CONR^aR^b$; and $R^a$ and $R^b$ independently represent hydrogen, $C_{1-6}$ alkyl, $C_{2-6}$ alkenyl, $C_{2-6}$ alkynyl, $C_{3-7}$ cycloalkyl, $C_{3-7}$ cycloalkyl($C_{1-6}$ alkyl), indanyl, phenyl, or phenyl($C_{1-6}$ alkyl).

2. The compound of claim 1 of the formula IIA, or a pharmaceutically acceptable salt thereof:

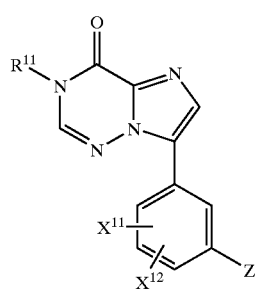

(IIA)

wherein:

$X^{11}$ represents hydrogen, fluoro, chloro, methyl, trifluoromethyl or methoxy;

$X^{12}$ represents hydrogen or fluoro;

$R^{11}$ represents a group selected from: $C_{1-6}$ alkyl, halo($C_{1-6}$)alkyl, dihalo($C_{1-6}$)alkyl, hydroxy($C_{1-6}$)alkyl, dihydroxy($C_{1-6}$)alkyl, $C_{1-6}$ alkoxy($C_{1-6}$)alkyl, di($C_{1-6}$) alkoxy($C_{1-6}$)alkyl, cyano($C_{1-6}$)alkyl, $C_{2-6}$ alkoxycarbonyl($C_{1-6}$)alkyl, $C_{3-7}$ cycloalkyl, pyridinyl, quinolinyl, isoquinolinyl, pyridazinyl, pyrimidinyl, pyrazinyl, furyl, benzofuryl, dibenzofuryl, thienyl, benzthienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl, tetrazolyl, furylmethyl, furylethyl, thienylmethyl, thienylethyl, oxazolylmethyl, oxazolylethyl, thiazolylmethyl, thiazolylethyl, imidazolylmethyl, imidazolylethyl, oxadiazolylmethyl, oxadiazolylethyl, thiadiazolylmethyl, thiadiazolylethyl, triazolylmethyl, triazolylethyl, tetrazolylmethyl, tetrazolylethyl, pyridinylmethyl, pyridinylethyl, pyrimidinylmethyl, pyrazinylmethyl, quinolinylmethyl, isoquinolinylmethyl, trifluoromethyl, formyl, $C_{2-6}$ alkylcarbonyl and $C_{2-6}$ alkoxycarbonyl;

Z represents a phenyl, pyridinyl, quinolinyl, isoquinolinyl, pyridazinyl, pyrimidinyl, pyrazinyl, furyl, benzofuryl, dibenzofuryl, thienyl, benzthienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl or tetrazolyl group, which group is unsubstituted or substituted with one or more substituents selected from: halogen, cyano, nitro, $C_{1-6}$ alkyl, hydroxy, $C_{1-6}$ alkoxy, oxy, $C_{1-6}$ alkylsulphonyl, amino, aminocarbonyl, formyl, $C_{2-6}$ alkoxycarbonyl and —$CR^a$=$NOR^b$;

$R^a$ and $R^b$ independently represent hydrogen, $C_{1-6}$ alkyl, $C_{2-6}$ alkenyl, $C_{2-6}$ alkynyl, $C_{3-7}$ cycloalkyl, $C_{3-7}$ cycloalkyl($C_{1-6}$ alkyl), indanyl, phenyl, or phenyl($C_{1-6}$ alkyl).

3. The compound of claim 2 of the formula IIB, or a pharmaceutically acceptable salt thereof:

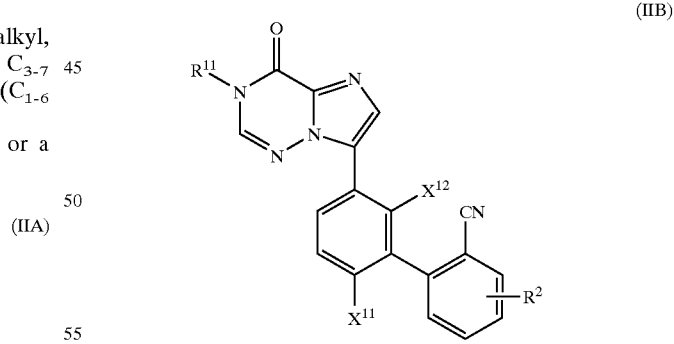

(IIB)

wherein:

$X^{11}$ represents hydrogen, fluoro, chloro, methyl, trifluoromethyl or methoxy;

$X^{12}$ represents hydrogen or fluoro;

$R^2$ represents hydrogen or fluoro;

$R^{11}$ represents methyl, ethyl, fluoroethyl, difluoroethyl or trifluoromethyl.

4. The compound of claim 2 of the formula IIC, or a pharmaceutically acceptable salt thereof:

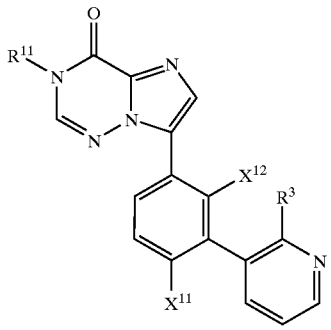

(IIC)

wherein:
X$^{11}$ represents hydrogen, fluoro, chloro, methyl, trifluoromethyl or methoxy;
X$^{12}$ represents hydrogen or fluoro;
R$^3$ represents hydrogen, fluoro, cyano or methyl;
R$^{11}$ represents methyl, ethyl, fluoroethyl, difluoroethyl or trifluoromethyl.

5. The compound of claim 2 formula IID, or a pharmaceutically acceptable salt thereof:

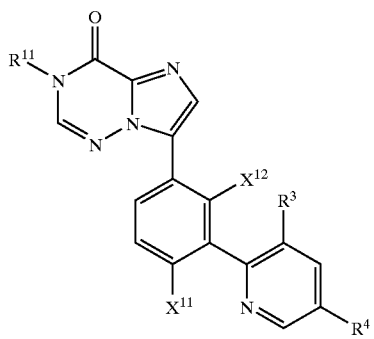

(IID)

wherein:
X$^{11}$ represents hydrogen, fluoro, chloro, methyl, trifluoromethyl or methoxy;
X$^{12}$ represents hydrogen or fluoro;
R$^4$ represents hydrogen or fluoro;
R$^{11}$ represents methyl, ethyl, fluoroethyl, difluoroethyl or trifluoromethyl.

6. A compound which is 4,2'-difluoro-5'-(3-methyl-4-oxo-3,4-dihydroimidazo[2,1-f][1,2,4]triazin-7-yl)biphenyl-2-carbonitrile or a pharmaceutically acceptable salt thereof.

7. A pharmaceutical composition comprising the compound of claim 1 or a pharmaceutically acceptable salt thereof and a pharmaceutically acceptable carrier.

8. A method for the treatment of anxiety which comprises administering to a patient in need of such treatment an effective amount of the compound of claim 1 or a pharmaceutically acceptable salt thereof.

9. A method for the treatment of convulsions which comprises administering to a patient in need of such treatment an effective amount of the compound of claim 1 or a pharmaceutically acceptable salt thereof.

10. A method for the treatment of a cognitive disorder which comprises administering to a patient in need of such treatment an effective amount of the compound of claim 1 or a pharmaceutically acceptable salt thereof.

11. A process for the preparation of the compound of claim 1 which comprises reacting a compound of formula III with a compound of formula IV:

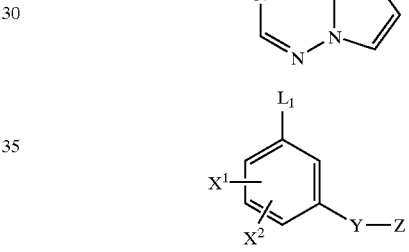

wherein X$^1$, X$^2$, Y, Z and R$^1$ are as defined in claim 1, and L$^1$ represents a suitable leaving group; in the presence of a transition metal catalyst.

* * * * *